(12) United States Patent
Pacey

(10) Patent No.: US 8,187,180 B2
(45) Date of Patent: May 29, 2012

(54) VIDEO RECTRACTOR

(75) Inventor: John A. Pacey, Vancouver (CA)

(73) Assignee: Verathon Medical (Canada) ULC, Burnaby, British Columbia (CA)

(*) Notice: Subject to any disclaimer, the term of this patent is extended or adjusted under 35 U.S.C. 154(b) by 611 days.

(21) Appl. No.: 11/397,944

(22) Filed: Apr. 3, 2006

(65) Prior Publication Data

US 2006/0276693 A1  Dec. 7, 2006

Related U.S. Application Data

(60) Provisional application No. 60/666,842, filed on Apr. 1, 2005.

(51) Int. Cl.
*A61B 1/06* (2006.01)
*A61B 1/267* (2006.01)

(52) U.S. Cl. .......... 600/245; 600/199; 600/186

(58) Field of Classification Search .......... 600/109, 600/185–246; 606/185–246
See application file for complete search history.

(56) References Cited

U.S. PATENT DOCUMENTS

| | | | | |
|---|---|---|---|---|
| 5,251,613 A * | 10/1993 | Adair | | 600/109 |
| 5,695,454 A * | 12/1997 | Mourkidou | | 600/186 |
| 5,707,382 A * | 1/1998 | Sierocuk et al. | | 606/190 |
| 5,738,628 A * | 4/1998 | Sierocuk et al. | | 600/104 |
| 5,827,178 A | 10/1998 | Berall | | |
| 5,842,973 A * | 12/1998 | Bullard | | 600/194 |
| 5,891,018 A * | 4/1999 | Wells | | 600/226 |
| 5,984,865 A | 11/1999 | Farley et al. | | |
| 6,083,151 A * | 7/2000 | Renner et al. | | 600/114 |
| 6,186,944 B1 * | 2/2001 | Tsai | | 600/200 |
| 6,543,447 B2 * | 4/2003 | Pacey | | 128/200.26 |
| 6,591,049 B2 * | 7/2003 | Williams et al. | | 385/123 |
| 6,652,453 B2 * | 11/2003 | Smith et al. | | 600/188 |
| 6,659,940 B2 * | 12/2003 | Adler | | 600/109 |
| 6,712,757 B2 | 3/2004 | Becker et al. | | |
| 7,871,375 B2 * | 1/2011 | Talieh | | 600/249 |
| 2001/0014768 A1 * | 8/2001 | Kaplan et al. | | 600/188 |
| 2002/0087050 A1 * | 7/2002 | Rudischhauser et al. | | 600/199 |
| 2003/0088156 A1 * | 5/2003 | Berci et al. | | 600/188 |
| 2003/0095781 A1 * | 5/2003 | Williams | | 385/146 |
| 2003/0181900 A1 | 9/2003 | Long | | |
| 2004/0082833 A1 | 4/2004 | Adler et al. | | |
| 2004/0230218 A1 * | 11/2004 | Criscuolo et al. | | 606/190 |
| 2005/0043590 A1 * | 2/2005 | Mazzei et al. | | 600/188 |
| 2005/0049462 A1 * | 3/2005 | Kanazawa | | 600/170 |
| 2006/0217596 A1 * | 9/2006 | Williams | | 600/245 |

OTHER PUBLICATIONS

International Search Report; PCT app. No. PCT/CA2006/000513; Jul. 4, 2006; 4 pages.

(Continued)

*Primary Examiner* — Eduardo C Robert
*Assistant Examiner* — Jacqueline Johanas
(74) *Attorney, Agent, or Firm* — Scott Born Foster Pepper PLLC

(57) ABSTRACT

A retractor with a video system that has a blade portion detachably secured thereto is disclosed. In one embodiment, the video system is sealed within the retractor during use so that it need not be sterilized between uses. The blade portion is either reusable, in which case only it needs to be sterilized between uses, or the blade portion is disposable, thereby further preventing inadvertent contamination of the patient. The video system can be detachably secured to a variety of different shaped blade portions, thereby allowing the retractor, with its single video system, to operate effectively as a straight or curved blade laryngoscope, anoscope, colposcope, and the like.

2 Claims, 5 Drawing Sheets

OTHER PUBLICATIONS

Written Opinion of the International Searching Authority; PCT app. No. PCT/CA2006/000513; Jul. 4, 2006; 7 pages.

Notification of Transmittal of the International Search Report; PCT app. No. PCT/CA2006/000513; Jul. 4, 2006; 1 page.

* cited by examiner

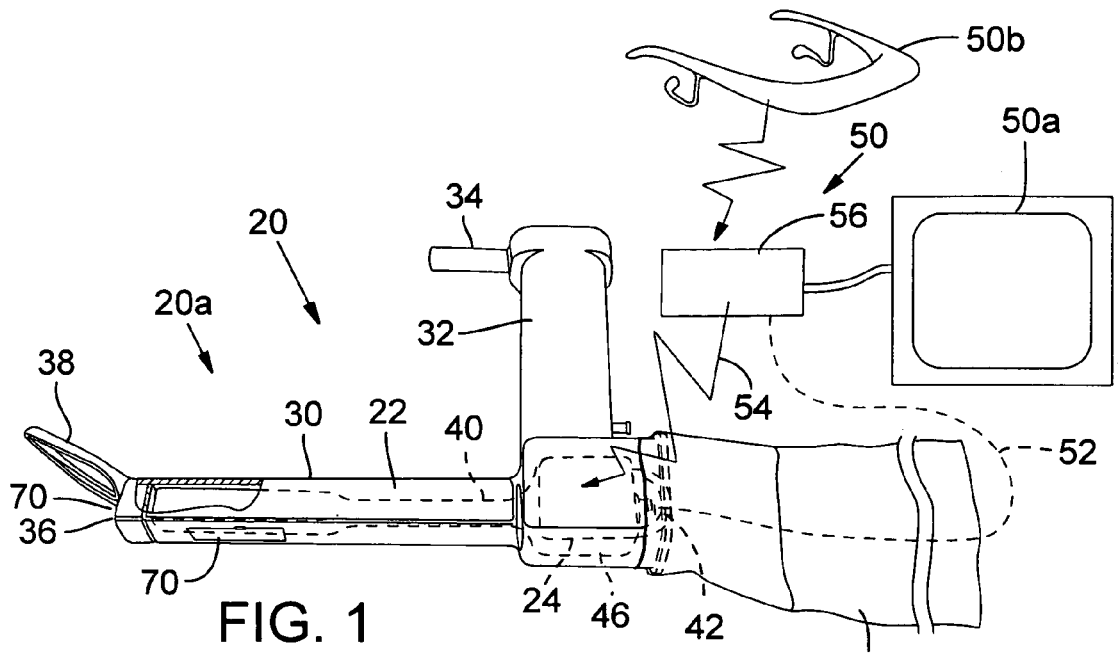
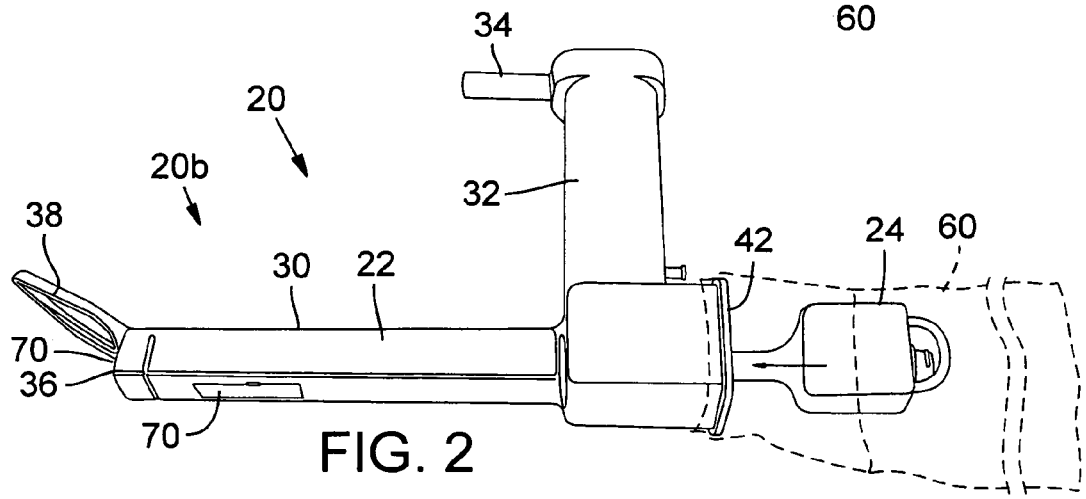
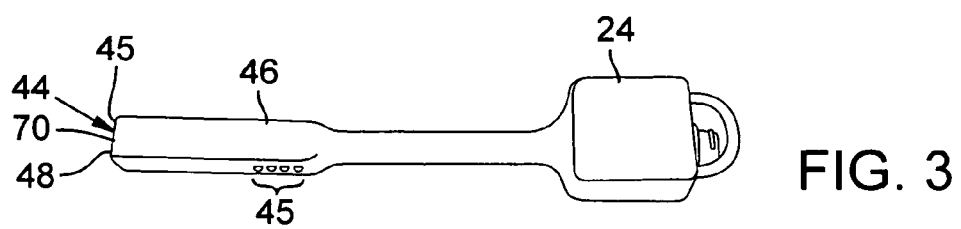

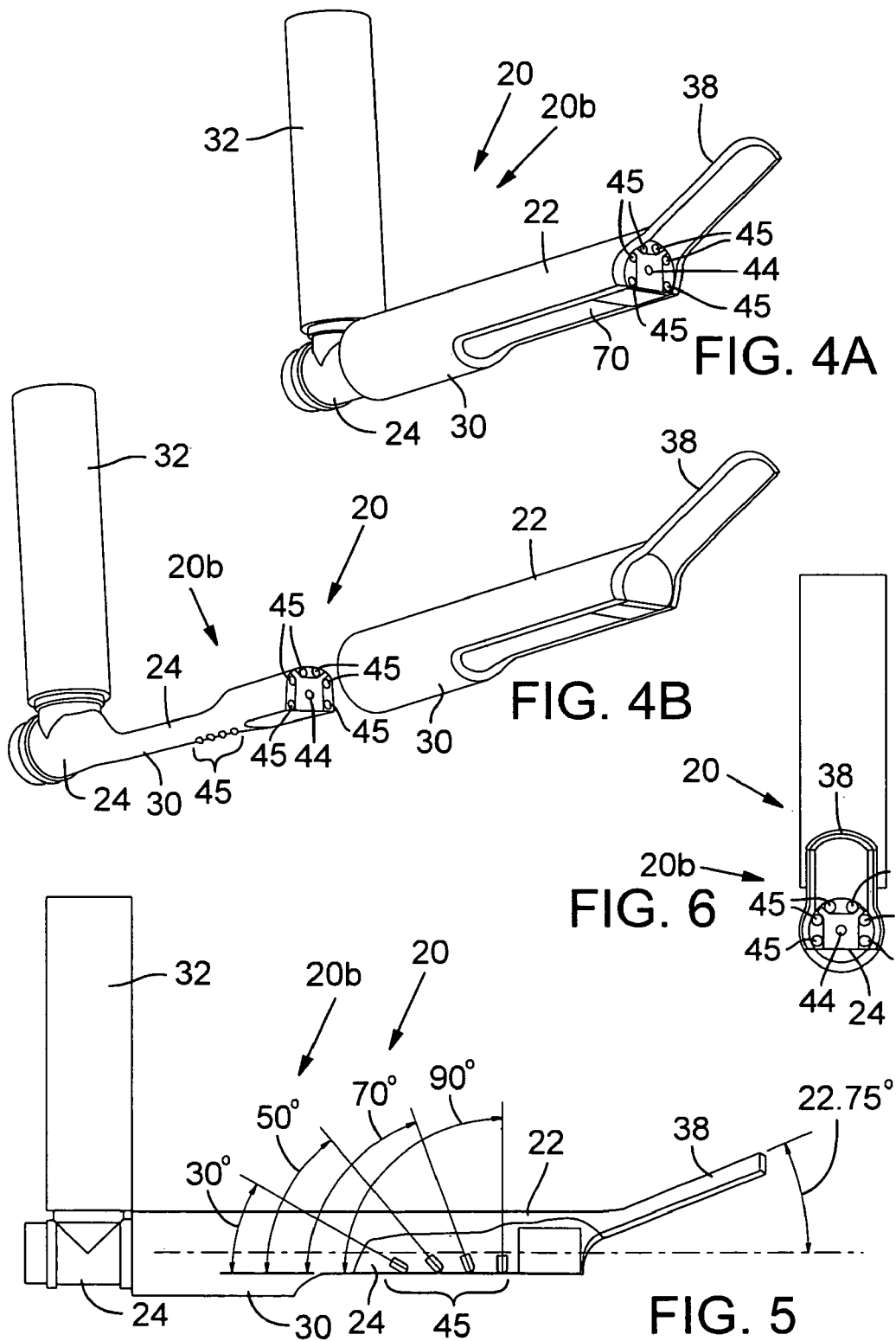

VIDEO RECTRACTOR

REFERENCE TO RELATED APPLICATIONS

This application claims priority to U.S. Provisional Application No. 60/666,842, filed on Apr. 1, 2005.

FIELD OF THE INVENTION

This invention relates to retractors used in the medical profession to permit controlled access and assist visibility during medical procedures and the like.

BACKGROUND

Retractors are probes used during medical procedures to provide the health care provider with controlled access to the patient and to assist with visibility of the area being treated. In general, a retractor has a control arm or blade portion that extends from a handle or base portion. The control arm or blade operably engages the area being treated, while the handle or base is used to position the control arm or blade as needed. The retractor can be hand-held by a health care provider or mounted to an examination table, operating table, or the like.

The shape of the retractor's blade portion often defines and limits its use. For example, a retractor's blade that is sized and shaped to fit down a patient's throat is often referred to as an intubation instrument or a laryngoscope. Similarly, specific use retractors, such as anoscopes and colposcopes, are retractors that have blades that are shaped to optimally engage specific areas of the patient.

Recently, efforts have been made to improve the effectiveness of some types of retractors by adding lighting and/or video systems. For example, U.S. Pat. No. 5,827,178 to Berall ("Berall") discloses mounting a camera in the vicinity of the distal end of the blade and a viewer mounted to the laryngoscope such that the practitioner has a simultaneous line of sight and camera view during insertion.

While such camera and lighting systems can improve the health care provider's viewing abilities of the patient, they have several drawbacks. For example, since most retractors must be sterilized prior to use, cameras, lights, and their related electronics that are secured to the retractor are regularly subjected to sterilization procedures. Over time, these procedures can tend to prematurely deteriorate these components thereby limiting their useful lives.

Similarly, since most retractors are monolithic structures having a blade that is sized and shaped for a single purpose, if a health care provider would like different use retractors to each have video and/or lighting systems, each type of retractor requires its own camera and/or lighting system to be mounted therein. Moreover, since blade sizes and shapes for a given use retractor, such as laryngoscopes, can vary, for example for use on adults and children, each different sized laryngoscope must have its own camera and/or lighting systems mounted thereto. Accordingly, despite the benefits associated with providing video and/or lighted retractors, the high number of cameras, lighting systems, their related electronic systems, and their related increased costs associated with maintaining them, significantly increases the overall costs of providing these systems to health care providers.

In addition, the camera system is out of service during cleaning cycles, which may impact its usefulness should an emergency need arise during the cleaning cycle.

SUMMARY OF THE INVENTION

The present invention overcomes these and other problems of known retractors. It provides a retractor with a video system that has a blade portion detachably secured thereto. Preferably, the video system is sealed within the retractor during use so that it need not be sterilized between uses.

The blade portion is either reusable, in which case only it needs to be sterilized between uses, or the blade portion is disposable, thereby further preventing inadvertent contamination of the patient. In one disclosed embodiment, the video system can be detachably secured to a variety of different shaped blade portions, thereby allowing the retractor, with its single video system, to operate effectively as a laryngoscope, anoscope, colposcope, and the like.

In one disclosed embodiment, the video system has a viewing device, which is preferably a Charged Coupled Device ("CCD") or Complementary Metal Oxide Semiconductor ("CMOS") camera positioned near the base end of a lifter portion of the blade portion, and aligned to provide a perspective view toward the distal end of the lifter. Lights, which are preferably Light Emitting Diode ("LED") units, are positioned around the camera and directed toward the distal end of the lifter to facilitate viewing. A transparent protective sheathing, such as clear plastic or the like, is preferably provided on the detachable blade portion over the camera lens and lights to seal the video system within the retractor, thereby preventing the need for the video system to be sterilized between uses.

The retractor can also provide a path for guiding movement of tools, such as suction devices or the like. In such case, the instrument includes a passage into which such instruments can be mounted.

Other advantages and features of the present invention will become clear upon study of the following portion of this specification and drawings.

BRIEF DESCRIPTION OF THE DRAWINGS

FIG. 1 is an isometric view of a retractor in accordance with an embodiment of the present invention showing a possible connection to a viewing system.

FIG. 2 is an isometric view of the retractor of FIG. 1 showing a possible detachable connection of a blade portion to a video system.

FIG. 3 is an isometric view of the video system of FIG. 2.

FIG. 4A is an isometric view of an alternative possible retractor embodiment in accordance with an embodiment of the present invention.

FIG. 4B is an exploded isometric view of the alternative possible retractor of FIG. 4A showing a variety of different shaped blade portions being detachably secured to the video portion.

FIG. 5 is a left, side view of the alternative possible retractor embodiment of FIG. 4.

FIG. 6 is a front view of the alternative possible retractor embodiment of FIG. 4.

DETAILED DESCRIPTION OF PREFERRED EMBODIMENTS

Figure 7A:
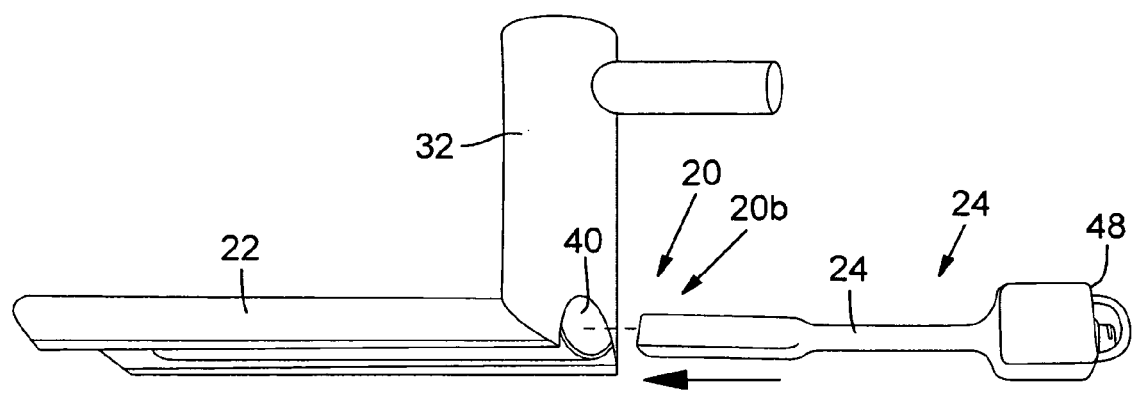
FIG. 7A is an isometric view of a retractor with a second possible blade portion operably secured to the video system of FIG. 3 thereby defining a video anoscope.
Figure 7B:
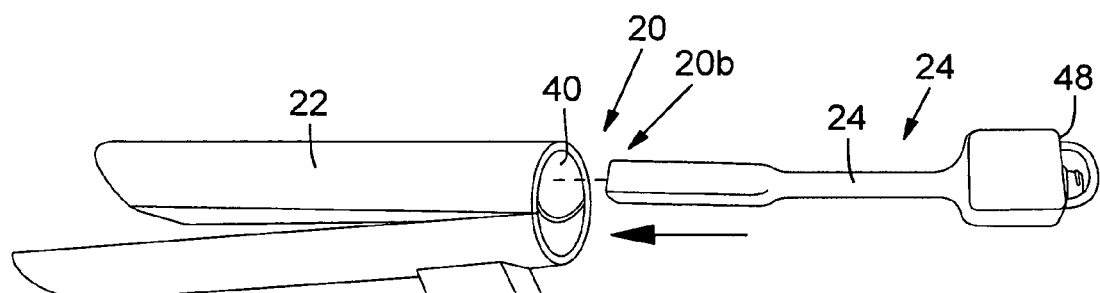
FIG. 7B is an isometric view of a retractor with a third possible blade portion operably secured to the video system of FIG. 3 thereby defining a video colposcope.
Figure 8:
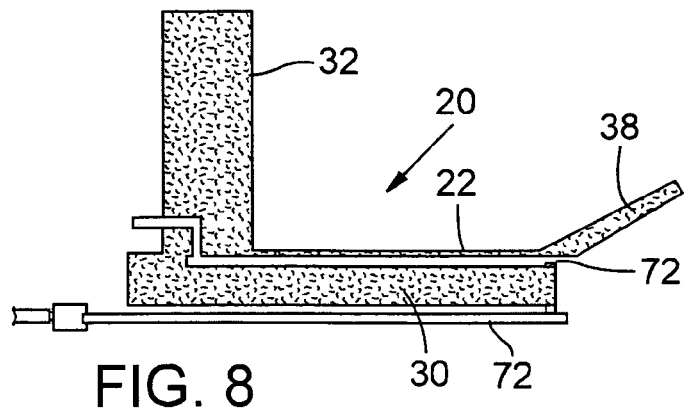
FIG. 8 is a cross sectional view of a possible retractor embodiment in accordance with an embodiment of the present invention.
Figure 9:
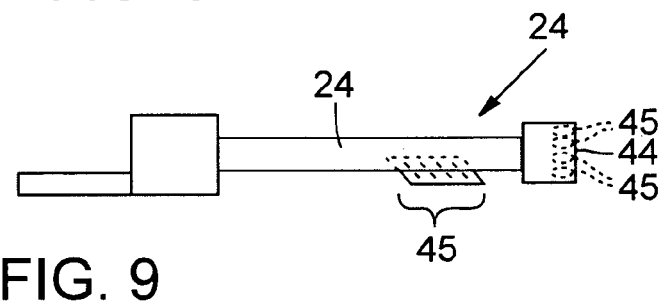
FIG. 9 is a schematic side view of a video system in accordance with an embodiment of the present invention.
Figure 11:
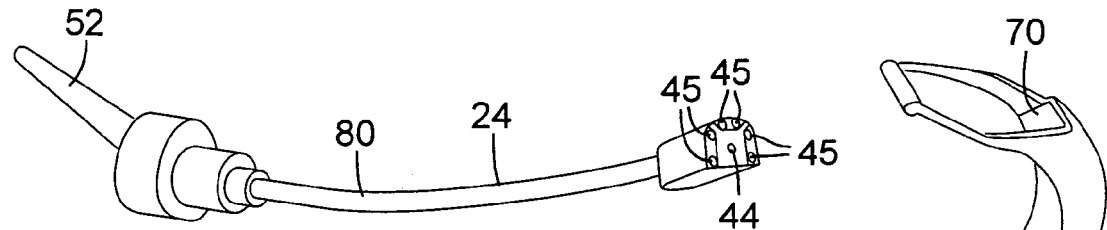
FIG. 11 is an isometric view of the video system of FIG. 10.
Figure 10:
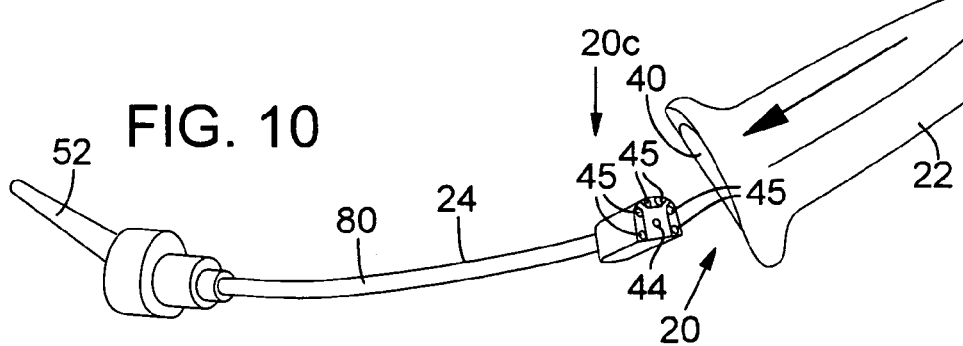
FIG. 10 is an isometric view of a retractor of the present invention showing a possible intubation instrument configuration with a blade portion detachably secured to a video system received therein with a portion of the blade portion cut-away to show internal detail.
Figure 12:
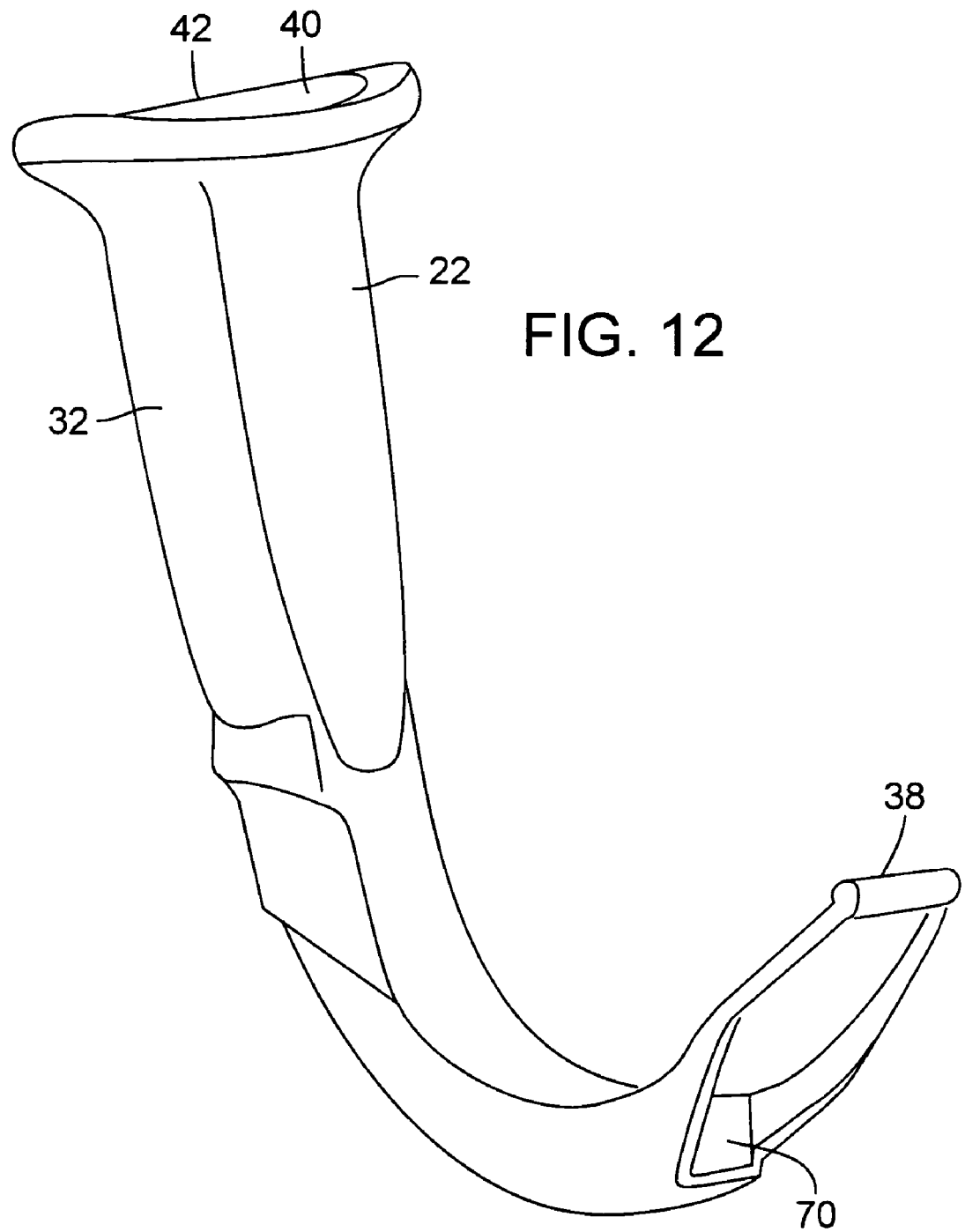
FIG. 12 is an isometric view of the blade portion of FIG. 10.

A retractor 20 having a blade portion 22 detachably secured to a video system 24 sealed therein is shown in FIGS. 1-12. In particular, FIGS. 1-3, 7A, 7B and 9 show a first preferred retractor embodiment 20a, FIGS. 4-7 show a second preferred retractor embodiment 20b, and FIGS. 10-12 show a third preferred retractor embodiment 20c. Alternative possible features are shown in FIG. 8. In order to avoid unnecessary repetition, common elements between these three embodiments 20a-c are like numbered.

A. First Preferred Embodiment

With particular reference to FIGS. 1-3, a first preferred retractor embodiment 20a is disclosed. The blade portion 22 has an elongated arm 30 with integrally attached handle 32. The blade portion 22 is preferably a monolithic structure formed with a material that can withstand repeated sterilization such as metal, rigid plastic, or the like. If desired, a rigid mounting pin 34 is also operably secured to the blade portion 22, preferably at the handle 32 as shown.

The elongate arm 30 has a distal end 36 that is inserted into the patient. An elongate lifter portion 38 preferably extends from the distal end 36 of the arm 30 at a desired defined angle. The arm 30 defines a chamber 40 therein for detachably receiving the video system 24 therein. Preferably, the chamber 40 is open at the end 42 of the arm 30 opposite the distal end 36 for allowing the video system 24 to be secured to the blade portion 22 therethrough as best shown in FIG. 2.

The video system 24 preferably includes a camera 44 operably secured within a frame portion 46. Preferably, the frame portion 46 is an elongate structure with the camera 44 directed outward from the distal end 48. More preferably, one or more lights 50, which are preferably Light Emitting Diodes ("LED") are positioned around the camera 44 and directed outward from the distal end 48 to facilitate operator viewing. Lights 45 are also preferably mounted along the length of the frame portion 46. The use of one or more LED cold light elements in front of the camera lens provide needed light without producing any heat. Accordingly, unlike traditional expensive Zenon lights typically used on fiber optic laryngoscopes, economical LED lights will not burn sensitive membranes.

The camera 44 is preferably a Complementary Metal Oxide Semiconductor ("CMOS") or Charged Coupled Device ("CCD") hybrid camera, both of which are more compact, light weight, light sensitive, and economical, than traditional cameras used in such applications. Known manufacturers and sellers of such cameras include Sun Microsystems, Amain Electronics, and Misumi Electronics.

Preferably, the camera 44 is operably connected to a power source, such as a battery or A/C connection, and suitable related electronics, which are stored in the frame portion 46 toward the opposite end 48 away from the camera 44.

As best shown in FIG. 1 the camera 44 is operably connected to a display system 50, either by a wired 52 or wireless 54 connection. Such connections can include a transmitter received within the frame portion 46 and the display system 50 includes a receiver 56 for receiving video signals from the transmitter. Alternatively, such a system can include infrared technology or the like. The camera 44 and related transmitter can also communicate with the display system 50, or other equipment such as remote locations via the evolving industry standard more commonly known as "bluetooth." Such communication can also be used to transmit the information via the Internet or the like, thereby facilitating real-time remote incident analysis, advice, assistance, and/or teaching.

The display system 50 may be detached from or attached to the retractor 20a, and may also be configured to simultaneously display other relevant information such as the patient's vital signs and the like, thereby facilitating operator use of the instrument. The display itself can be through a conventional monitor 50a and/or through monitor glasses 50b worn by one or more of the health care providers.

Preferably, the camera 44 and frame portions 46 are secured within a sealed chamber of the arm 30, thereby preserving the sterility of the outer surface of the arm 30 without requiring sterilization of the video system 24. More preferably, a protective sleeve 60 (FIGS. 1 & 2) extends from the open end 42 in the arm 30 to perverse the exterior sterility of the system. Preferably, the CMOS or CCD camera body is also sealed within the frame portion 46.

A transparent protective sheath 70 is preferably positioned on the arm 30 adjacent to the camera 44 and any lights 45 found on the frame portion 46 thereby making windows through which the camera 44 and lights 45 are directed. Preferably, the sheath is a transparent polymer, such as plastic, which sheds mucus and blood, has little tendency to fog during use, and equilibrates rapidly to airway temperature.

The instrument may also include paths (not shown) for transmitting oxygen and/or fluid to the camera lens, thereby assisting clearing and cleaning the lens during operation.

Referring to FIG. 8, this embodiment can also include one or more guide paths 72 for slidably receiving medical devices such as suction tubes, cauterization lasers, and the like therethrough. In such case, a protective sleeve 60 is operably secured to the retractor 20a as shown in FIG. 1 to preserve sterilization of the exterior environment without necessarily requiring sterilization of the interior surfaces.

If desired, a defogger assembly that defogs the lens of the camera by heating the lens is disclosed. One such structure for heating the lens includes thermally-coupling a heating element, such as a resistor or coil, to the lens of the camera. For example, the resistor is preferably positioned adjacent to the lens and placed in electrical communication with a power source. Preferably, the components of the defogger assembly, such as the power source, heating element, and related wiring, are contained within the frame. More preferably, the power source is a low voltage direct current battery or the like.

The resistor and current are selected so as to heat the lens to a desired temperature to permit defogging, while still preventing the resistor from becoming hot enough to burn a patient or damage any components of the instrument. Preferably, the heating element is regulated so as to maintain an optimal temperature. For example, a thermostat operably secured to the defogger assembly can modulate current from the power source based on the level of detected temperature so as to prevent the heating element from becoming too hot.

Preferably, a switch is operably secured to the resistor such that power to the heating element may be turned on or off as needed to defog the lens of the viewer by heating the lens. The switch may be manually controlled or controlled by internal electronics so as to activate under predetermined conditions. For example, in cases where the viewer is an electronically actuated camera, the internal electronics can power the heating element whenever the camera is activated. Alternatively, in cases where the instrument includes a light source, the defogger assembly can be activated whenever the light source is activated, for example, by activating light switch.

Referring to FIGS. 7A and 7B, it can be appreciated that the video system 24 of FIG. 3 can be inserted into different shaped blade portions 22 to define different instruments. For example, in FIG. 7A, the blade portion 22 is shaped like a conventional anoscope blade 22a, thereby allowing the retractor 20a to serve as a video anoscope. Similarly, in FIG. 7B, the blade portion 22 is shaped like a conventional colposcope blade 22b, thereby allowing the retractor 20a to serve as a video colposcope.

B. Second Preferred Embodiment

Referring to FIGS. 4A-6, an alternative preferred retractor embodiment 20b is disclosed. In this embodiment, the frame containing the video system also defines the handle of the retractor 20. The detachable blade portion 22 includes a lifter 38 and a transparent protective sheath 70 through which the camera 44 and lights 45 are directed as shown. Preferably, the distal end of the frame portion 46 includes a plurality of lights 45 surrounding the camera 44. Moreover, a plurality of lights 45 are angled and aligned as shown along the shaft of the frame portion 46 to allow additional lighting during use of the retractor 20b.

The lens heating system and the protective sleeve of the first embodiment can be operably secured thereto. Moreover, the video system 24 can be in wireless and/or wired communication with a display system 50 of FIG. 1.

Preferably, the blade portion 22 is a monolithic structure that is easily sterilized. More preferably, the blade portion 22 is formed of an economical material, such as molded polymer and the like, thereby making the blade portion disposable and/or reusable as desired.

C. Third Preferred Embodiment

With particular reference to FIGS. 9-11, a third preferred retractor embodiment 20c of a retractor 20 is disclosed. The blade portion 22 is formed of an economical easy to sterilize material, such as molded polymer and the like, and shaped like a conventional curved-blade intubation instrument. The video system 24 includes a camera and lighting mounted on the distal end of an elongate flexible frame portion 80. Accordingly, the distal end 48 of the flexible frame portion 80 can be slidably received within a recess in the blade portion 22 as shown to allow the camera 44 to align with a substantially transparent window 82 in the blade portion 22. After use of the intubation instrument, the video system 24 can be detached from the blade portion 22, thereby allowing the blade portion 22 to be sterilized without necessarily requiring sterilization of the video system 24.

While the present invention has been described in terms of preferred embodiments, it will be appreciated by one of ordinary skill that the spirit and scope of the invention is not limited to those embodiments, but extend to the various modifications and equivalents as defined in the appended claims. For example, other types of cameras 44 and lights 45 could be used. Moreover, additional channels could be provided in the blade portions for delivering other devices to the distal end of the instrument.

What is claimed is:

1. A retractor, comprising:
   an elongate blade comprising:
   a plurality of surfaces defining a chamber within the elongate blade, wherein the plurality of surfaces includes a distal surface comprising a first substantially transparent window, and
   an elongate lifter portion that extends from a distal end of the elongate blade;
   a video system having a camera mounted on the distal end of an elongate flexible frame portion within the chamber of the elongate blade, said video system detachably secured within the chamber such that said camera is aimed through said first transparent window, whereby the video system is sealed within the chamber of the elongate blade during use; and
   one or more lights positioned around the camera, whereby when the camera is detachably secured within the chamber, the one or more lights are directed outward from the distal end, and whereby a second light of the one or more lights is operably located proximally to a first light of the one or more lights and secured to said video system, said first light aimed in a first direction, said second light aimed in a second direction substantially perpendicular to said first direction, and wherein a second surface of the plurality of surfaces comprises a second substantially transparent window through which said second light is aimed when said video system is mounted within the chamber.

2. The retractor of claim 1, further including a third light of the one or more lights is located proximally to the second light and operably secured to said video system, said third light aimed in a third direction at an angle relative to said second direction.

\* \* \* \* \*